US012746216B2

(12) United States Patent
Jonkergouw et al.

(10) Patent No.: US 12,746,216 B2
(45) Date of Patent: Sep. 29, 2026

(54) COMBINATORY TREATMENT

(71) Applicant: ARIVIN THERAPEUTICS OY, Helsinki (FI)

(72) Inventors: Christopher Jonkergouw, Aalto (FI); Ekaterina Osmekhina, Aalto (FI); Markus Linder, Aalto (FI); Katarzyna Leskinen, Helsingin Yiopisto (FI); Päivi Saavalainen, Helsingin Yiopisto (FI)

(73) Assignee: ARIVIN THERAPEUTICS OY, Helsinki (FI)

( * ) Notice: Subject to any disclaimer, the term of this patent is extended or adjusted under 35 U.S.C. 154(b) by 827 days.

(21) Appl. No.: 17/917,338

(22) PCT Filed: Apr. 7, 2021

(86) PCT No.: PCT/FI2021/050255

§ 371 (c)(1),
(2) Date: Oct. 6, 2022

(87) PCT Pub. No.: WO2021/205075

PCT Pub. Date: Oct. 14, 2021

(65) Prior Publication Data

US 2023/0145342 A1 May 11, 2023

(30) Foreign Application Priority Data

Apr. 7, 2020 (FI) ..................................... 20205369

(51) Int. Cl.
*A61K 31/05* (2006.01)
*A61K 31/04* (2006.01)
(Continued)

(52) U.S. Cl.
CPC ............ *A61K 31/05* (2013.01); *A61K 31/407* (2013.01); *A61K 31/427* (2013.01);
(Continued)

(58) Field of Classification Search
CPC .... A61K 31/05; A61K 31/407; A61K 31/427; A61K 31/5383; A61K 31/546; A61K 31/7036; A61K 38/12; A61P 31/04
See application file for complete search history.

(56) References Cited

U.S. PATENT DOCUMENTS

2014/0066365 A1 3/2014 Grare et al.

FOREIGN PATENT DOCUMENTS

| | | | | |
|---|---|---|---|---|
| WO | 2009058327 A1 | 5/2009 | | |
| WO | 2015188140 A1 | 12/2015 | | |
| WO | WO-2017025951 A1 * | 2/2017 | .............. | A61P 31/04 |

OTHER PUBLICATIONS

Barbera, Lucia, et al. "A water-soluble pillar [5] arene as a new carrier for an old drug." Organic & Biomolecular Chemistry 15.15 ( 2017): 3192-3195. (Year: 2017).*

(Continued)

*Primary Examiner* — James H Alstrum-Acevedo
*Assistant Examiner* — Justin Christopher Sanchez
(74) *Attorney, Agent, or Firm* — Meunier Carlin & Curfman LLC

(57) ABSTRACT

This invention relates to use of a macrocyclic cavity-containing compound sensitizing a microbe towards an antimicrobial agent. The invention also relates to use of a macrocyclic cavity-containing compound in reducing the amount of an antimicrobial agent needed to prevent or inhibit the growth of a microbe in a subject. Further, the invention relates to use of a macrocyclic cavity-containing compound in reducing the build-up of resistance of a microbe towards an anti-microbial agent. The invention also relates to a macrocyclic cavity-containing compound and an antimicrobial agent for use in inhibiting/treating/preventing a microbial infection in a subject having a microbial infection or being at risk of a microbial infection.

14 Claims, 12 Drawing Sheets
(12 of 12 Drawing Sheet(s) Filed in Color)

(51) Int. Cl.
*A61K 31/407* (2006.01)
*A61K 31/427* (2006.01)
*A61K 31/5383* (2006.01)
*A61K 31/546* (2006.01)
*A61K 31/7036* (2006.01)
*A61K 38/12* (2006.01)
*A61P 31/04* (2006.01)

(52) U.S. Cl.
CPC ........ *A61K 31/5383* (2013.01); *A61K 31/546* (2013.01); *A61K 31/7036* (2013.01); *A61K 38/12* (2013.01); *A61P 31/04* (2018.01)

(56) References Cited

OTHER PUBLICATIONS

Furukawa SKuchma SL, O'Toole GA 2006. Keeping Their Options Open: Acute versus Persistent Infections. J Bacteriol 188:. (Year: 2006).*

Garcia Jimenez D, Poongavanam V, Kihlberg J. Macrocycles in Drug DiscoveryâLearning from the Past for the Future. J Med Chem. Apr. 27, 2023;66(8):5377-5396. (Year: 2023).*

Tursun, E.G., Bozok, T. & Aslan, G. Antimicrobial resistance mechanisms in non-tuberculous mycobacteria. Folia Microbiol (2025). (Year: 2025).*

International Search Report and Written Opinion in International Application No. PCT/FI2021/050255, mailed Jun. 30, 2021, 17 pages.

Search Report in Finnish Application No. 20205369, dated Nov. 13, 2020, 2 pages.

Arnab Dawn: "Multifaceted Supramolecular Interactions from C-Methylresorcin[4]arene Lead to an Enhancement in In Vitro Antibacterial Activity of Gatifloxacin—Dawn—2017—Chemistry—A European Journal—Wiley Online Library", Chemistry—A European Journal, vol. 23, No. 72' Dec. 22, 2017 (Dec. 22, 2017), pp. 18171-18179.

Barbera Lucia et al: "A water-soluble pillar[5]arene as a new carrier for an old drug". Organic & Biomolecular Chemistry, [Online] vol. 15. No. 15. Jan. 1, 2017 (Jan. 1, 2017), pp. 3192-3195.

Nial J Wheate et al: "Host-guest complexes of the antituberculosis drugs pvrazinamide and isoniazid with cucurbit7luril", Journal of Inclusion Phenomena and Macrocyclic Chemistry, Kluwer Academic Publishers, DO, vol. 68. No. 3-4. May 12, 2010 (May 12, 2010), pp. 359-367.

Athanassiou G et al: "Antimicrobial activity of beta-lactam antibiotics against clinical pathogensafter molecular inclusion in several cyclodextrins. A novel approach to bacterial resistance", Pharmaceutical and Clinical Research, John Wiley & Sons Ltd, London, GB, vol. 55, No. 3, Mar. 1, 2003 (Mar. 1, 2003), pp. 291-300.

Gao, L. et al. Positively Charged Nanoaggregates Based on Zwitter ionic Pillar-[5]arene that Combat Planktonic Bacteria and Disrupt Biofilms. In: Angew. Chem. Int. Ed. 2019, vol. 58, 3645-3649 <DOI:10.1002/anie.201810314>.

Joseph, R. et al. Cationic Pillararenes Potently Inhibit Biofilm Formation without Affecting Bacterial Growth and Viability. In: J. Am. Chem. Soc. Jan. 8, 2016, vol. 138, 754-757, <DOI:10.1021/jacs.5b11834>.

Patel, M.B. et al. Hydraphiles enhance antimicrobial potency against *Eschericia coli*, Pseudomonas aeruginosa, and Bacillus subtulis . In: Bioorg. Med. Chem. 2016, vol. 24, 2864-2870, <DOI:10.1016/j.bmc.2016.04.058>.

* cited by examiner

COMBINATORY TREATMENT

FIELD OF THE INVENTION

This invention relates to use of a macrocyclic cavity-containing compound in sensitizing a microbe towards an antimicrobial agent. The invention also relates to use of a macrocyclic cavity-containing compound in reducing the amount of an antimicrobial agent needed to prevent or inhibit the growth of a microbe in a subject. In addition, the invention relates to use of a macrocyclic cavity-containing compound in reducing the amount of an antimicrobial agent needed to kill pathogenic microbes in a subject. The invention also relates to use of a macrocyclic cavity-containing compound in prolonging the administration interval of an antimicrobial agent needed to induce bacteriostatic or bactericidal effects on a microbe in a subject. Further, the invention relates to use of a macrocyclic cavity-containing compound in reducing the build-up of resistance of a microbe towards an anti-microbial agent. The invention also relates to a macrocyclic cavity-containing compound and an antimicrobial agent for use in inhibiting and/or treating and/or preventing a microbial infection in a subject having a microbial infection or being at risk of a microbial infection. Further, the invention relates to a macrocyclic cavity-containing compound and an antimicrobial agent for use in inhibiting, treating and/or preventing the formation of biofilm by pathogenic bacteria in a subject.

BACKGROUND OF THE INVENTION

The buildup of rapid resistance to antibiotics is one of the biggest global health problems we currently face. Combined with a 35 year innovation gap during which no new class of antibiotics have been found, the lack of antibiotics have resulted in forecasts where antibiotic resistant infections will become the most deadly cause in the world (by 2050) and have a huge economic impact. Multidrug resistance is so important, that the World Health Organization (WHO) has issued a global priority pathogens list of antibiotic resistance (WHO, 2017).

Since their first discovery, antibiotics quickly became the sole method of treating nearly all bacterial infections. Reports of resistance have followed antibiotics very soon after their discovery, but because of the continuous development of novel types of antibiotics, antibiotic resistance never received much attention. However, because of the innovation gap, excessive use in feedstock, wrong prescriptions and many other reasons, bacteria have caught up rapidly. To illustrate, *Pseudomonas aeruginosa* is known the one of the most problematic pathogens. Indeed, in a laboratory environment, *P. aeruginosa* is resistant to nearly all antibiotics within a period of 3 to 4 days.

The publications and other materials referred herein to illuminate the background of the invention, and in particular, cases to provide additional details respecting the practice, are incorporated by reference.

BRIEF DESCRIPTION OF THE INVENTION

The present invention relates to use of a macrocyclic cavity-containing compound in sensitizing a microbe towards an antimicrobial agent and/or in sensitizing a microbe to be susceptible to an antimicrobial agent. The present invention relates also to use of a macrocyclic cavity-containing compound in reducing the amount of an antimicrobial agent needed to induce bacteriostatic or bactericidal effects on a microbe in a subject. The invention also relates to use of a macrocyclic cavity-containing compound in prolonging the administration interval of an antimicrobial agent needed to induce bacteriostatic or bactericidal effects on a microbe in a subject. In addition, the present invention relates to use of a macrocyclic cavity-containing compound in reducing the build-up of resistance of a microbe towards an antimicrobial agent. The present invention relates to the use of a macrocyclic cavity-containing compound and an antimicrobial agent in inhibiting the growth of a microbe in a subject. The present invention relates also to use of a macrocyclic cavity-containing compound and an antimicrobial agent in inhibiting and/or treating and/or preventing a microbial infection in a subject having a microbial infection or being at risk of a microbial infection. The invention relates also to use of a macrocyclic cavity-containing compound and an antimicrobial agent in inhibiting, treating and/or preventing the formation of biofilm by pathogenic bacteria in a subject.

The invention also relates to a macrocyclic cavity-containing compound and an antimicrobial agent for use in inhibiting and/or treating and/or preventing a microbial infection in a subject having a microbial infection or being at risk of a microbial infection. Further, the invention relates to a macrocyclic cavity-containing compound and an antimicrobial agent for use in inhibiting, treating and/or preventing the formation of biofilm by pathogenic bacteria in a subject.

The present invention relates to a method of sensitizing a microbe towards an antimicrobial agent and/or in sensitizing a microbe to become susceptible to an antimicrobial agent by administrating a macrocyclic cavity-containing compound and an antimicrobial agent to a subject or by exposing the microbe to a macrocyclic cavity-containing compound and an antimicrobial agent. The present invention relates also to a method of reducing the build-up of resistance of a microbe towards an antimicrobial agent by exposing the microbe to a macrocyclic cavity-containing compound. In addition, the present invention relates to a method of reducing the amount of an antimicrobial agent needed to prevent or inhibit the growth of a microbe in a subject by administrating a macrocyclic cavity-containing compound and the antimicrobial agent to the subject. The present invention relates to a method of reducing the amount of an antimicrobial agent needed to kill pathogenic microbes in a subject by administrating a macrocyclic cavity-containing compound and the antimicrobial agent to the subject. The present invention relates also to a method of prolonging the administration interval of an antimicrobial agent needed to induce bacteriostatic or bacteriocidal effect on a microbe by administrating a macrocyclic cavity-containing compound and the antimicrobial agent to the subject. The present invention relates to a method of inhibiting growth of a microbe in a subject by administering a macrocyclic cavity-containing compound and an antimicrobial agent to the subject. The present invention also relates to a method of inhibiting and/or treating and/or preventing a microbial infection in a subject having a microbial infection or being at risk of a microbial infection by administrating an antimicrobial agent, and a macrocyclic cavity-containing compound to the subject. In addition, the present invention relates to a method of inhibiting, treating and/or preventing the formation of biofilm by pathogenic microbes in a subject by administrating a macrocyclic cavity-containing compound and an antimicrobial agent to the subject.

The present invention relates to a combined use of a macrocyclic cavity-containing compound and an antimicrobial agent to prevent or inhibit and/or treat a microbial infection in a subject. The present invention relates also to composition or a dosage form or a kit comprising a macrocyclic cavity-containing compound and an antimicrobial agent.

The objects of the invention are achieved by compounds, uses and methods characterized by what is stated in the independent claims. The preferred embodiments of the invention are disclosed in the dependent claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
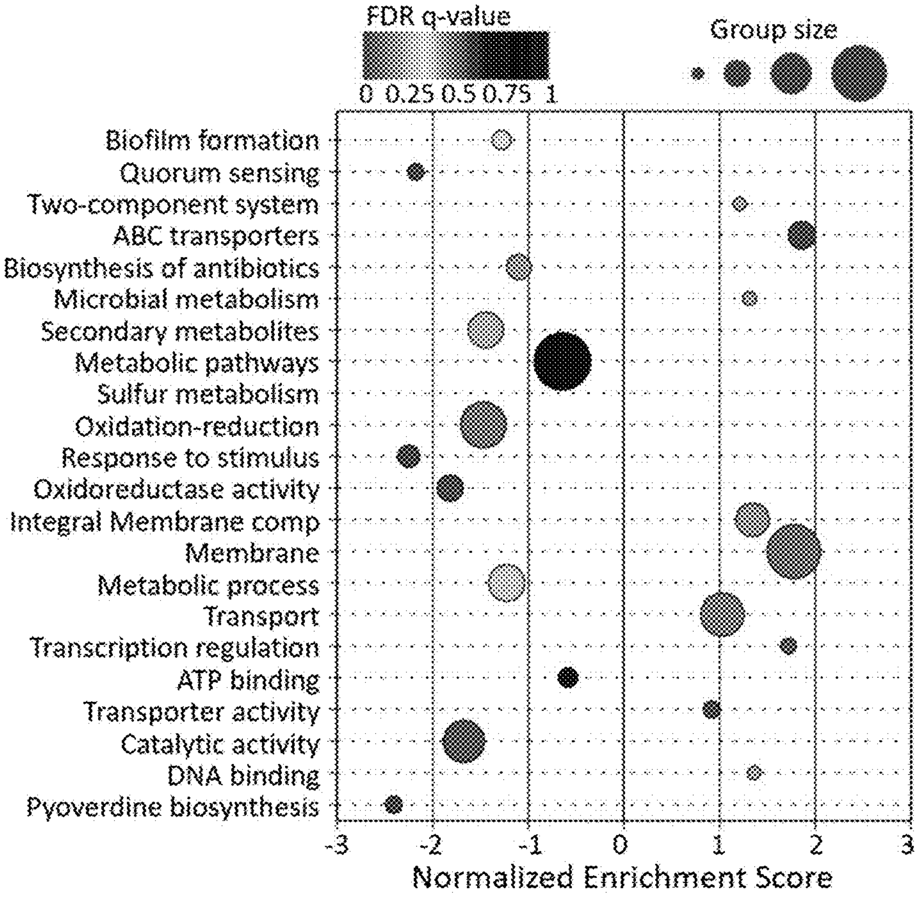
FIG. 1 shows the Gene Set Enrichment Analysis (GSEA) on the effect of P[5]a against KEGG and GO gene sets. Changes in gene expression levels are grouped in specific "gene sets", which group all genes related to a specific function, for instance biofilm formation. This ranking conveniently shows the effect of a treatment on specific phenotypic effects, rather than individual genes.

Unless otherwise specified, the terms used in the description and claims have the meanings known to a person skilled in the art.

In the present specification, the term "macrocyclic cavity-containing compound" refers to an organic cyclic compound forming cylindrical structure providing a cavity for host-guest interaction. The macrocyclic cavity-containing compound inhibits a microbial signalling molecule or reduces the amount of a microbial signalling molecule by binding the microbial signalling molecule by non-covalent host-guest bonding. The macrocyclic cavity-containing compounds have been found to prevent or treat a microbial signaling molecule dependent and/or mediated microbial infection by binding the microbial signaling molecule by non-covalent host-quest bonding. In addition, the macrocyclic cavity-containing compounds bind specific components of the biofilm matrix. As a result, the microbes stop or reduce the production of one or several of toxins, biofilms and other virulence factors. Thus, the macrocyclic cavity-containing compounds act as virulence inhibitors and this mode of action differs significantly from antibiotics, which either inhibit growth of the pathogens or kill the pathogens. The macrocyclic cavity-containing compounds have no negative growth effects on microbes. Thus, the microbial cells are not under a pressure for survival and are less likely to gain and/or build up resistance. The host-guest binding of a macrocyclic cavity-containing compound and a microbial signalling molecule is solely an extracellular process. The macrocyclic cavity-containing compounds are too large to enter the microbial cells, which further reduces the chances of resistance development in microbes. The macrocyclic cavity-containing compounds do not affect the viability of the microbial cells. Further, they do not affect the viability of the animal cells.

The microbial signalling molecules or the quorum sensing (QS) molecules, are a group of small diffusible molecules, which bacteria can sense and release and which are utilized as a form of communication. In bacteria, especially in many Gram-negative pathogens, the signalling molecules regulate a wide variety of virulence associated factors, such as biofilm formation, the production of exotoxins and surfactants, motility, and nutrient scavenging molecules, as a means to increase chances of successful infections. In one embodiment, the microbial signalling molecule is a microbial quorum sensing signal molecule. In one embodiment, the microbial signalling molecule or the microbial quorum sensing signal molecule is homoserine lactone (HSL) and/or N-acyl-homoserine lactone (AHL). In one embodiment, the carbon chain of the HSL or the AHL has a length of 4 to 18 or 6 to 14 carbon atoms. In one embodiment, the carbon chain of the HSL or the AHL is linear. In one embodiment, the carbon chain of the HSL or the AHL is branched. In one embodiment, the macrocyclic cationic cavity-containing compound is also able to interact with extracellular DNA in the extrapolymeric substance.

Examples of such macrocyclic cavity-containing compounds are pillararenes, cucurbiturils, crown ethers, cyclodextrins, and calixarenes.

The present invention is based on a finding that a macrocyclic cavity-containing compound, called pillar[5]arene (P[5]a), with an antimicrobial agent was found to sensitize the bacteria i.e., making them more susceptible for the antimicrobial agent. Accordingly, antimicrobial agents to which bacteria used to be resistant were effective again when used together with a macrocyclic cavity-containing compound, such as P[5]a. Further, it was found that less antimicrobial agent was needed to be effective in inhibiting the growth of a microbe or to kill the microbe when used together with a macrocyclic cavity-containing compound, such as P[5]a, than without a macrocyclic cavity-containing compound. It was also found that the buildup of resistance to an antimicrobial agent by the pathogens is significantly reduced when a macrocyclic cavity-containing compound, such as P[5]a, is used with the antimicrobial agent. A macrocyclic cavity-containing compound, such as P[5]a, was found to function with a wide range of antimicrobial agents. The macrocyclic cavity-containing compound, such as P[5]a, was also found to be well tolerated, enabling a combined treatment with a wide variety of antibiotics.

Figure 12:
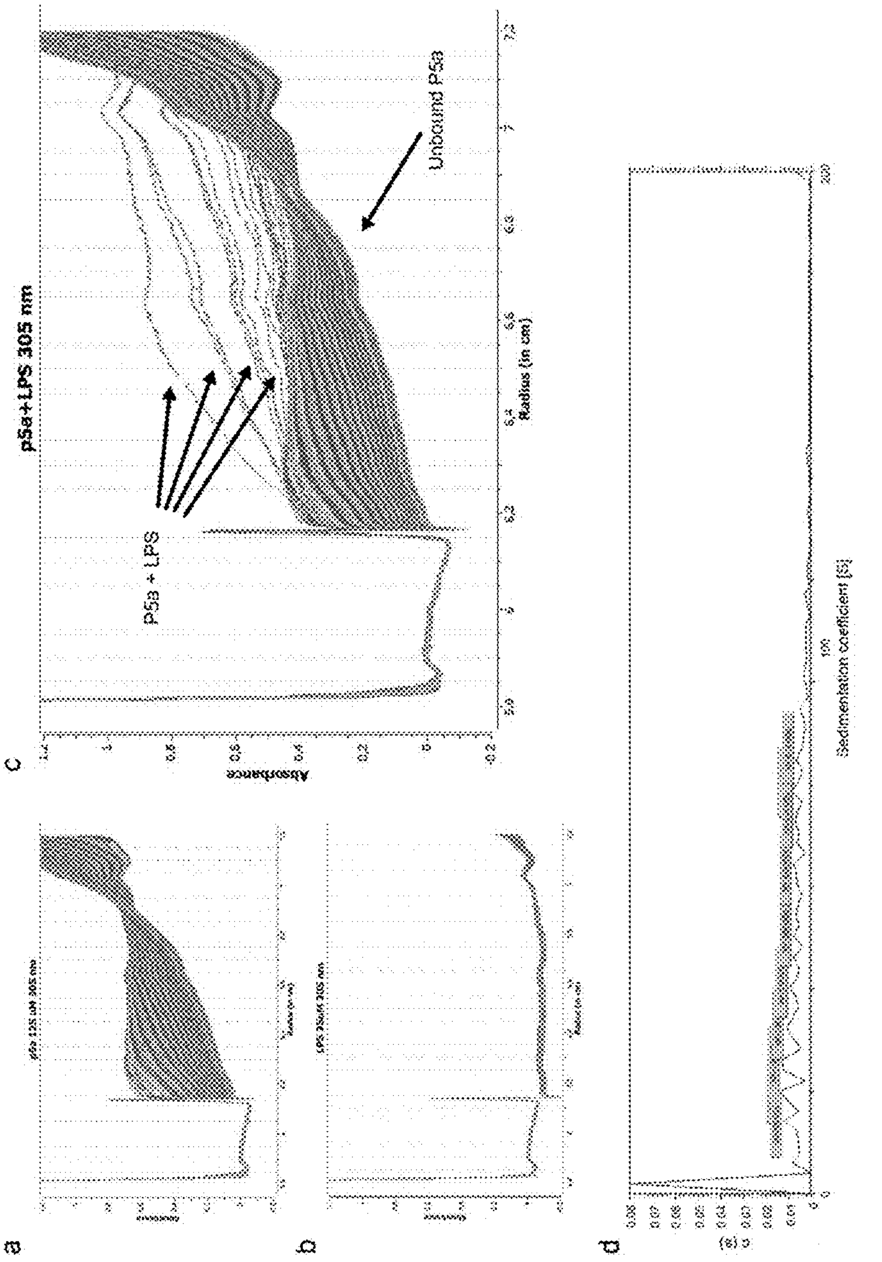
FIG. 12 shows the interaction of P[5]a with lipopolysaccharides of *P. aeruginosa*, strain PA10. a, Analytical ultracentrifuge sedimentation velocity analysis of P[5]a alone shows steady sedimentation profile at 305 nm. b, Analytical ultracentrifuge sedimentation velocity analysis of LPS alone shows no detectable sedimentation profile at 305 nm, which shows that at 305 nm, the sedimentation of P[5]a. is only followed. c, Analytical ultracentrifuge sedimentation velocity analysis of P[5]a together with LPS shows a very rapid and varying sedimentation profile at 305 nm, showing P[5]a-LPS complexes (indicated by arrows). This is followed by a large amount of unbound P[5]a, sedimenting slower (indicated by arrow). d, Molecular weight distribution of sedimentation profiles, strong interaction between 135 μM P[5]a and 35 μM LPS in UV absorbance at 305 nm. A clear initial peak of unbound P[5]a can be observer at low molecular weight (2260 Da), followed by a long and polydisperse collection of peaks, ranging from low molecular weight (S), to very high molecular weight (60.000 kDa) See Example 6.

The macrocyclic cavity-containing compounds were found to have a dual mechanism of action on Gram-negative micro-organisms. Firstly, they were found to attenuate the virulence through binding of microbial signaling molecules inside the inner cavity of the molecule. Secondly, they were found to sensitize bacterial outer membrane by the positively charged functional side groups. Specifically, pillar[5]arene, a macrocyclic cavity-containing compound, was found to attenuate virulence through binding of homoserine lactone (HSL) signaling molecules inside its inner cavity and to sensitize the bacterial outer membrane by binding the lipopolysaccharides (LPSs) of the bacterial outermembrane by its positively charged functional side groups. The strong interaction of a macrocyclic cavity-containing compound, P[5]a, with lipopolysaccharides of *P. aeruginosa*, strain PA10 is shown in FIG. 12 by the analytical ultracentrifuge analysis. The results indicate that P[5]a can interact with multiple LPS units, and might even act as a scaffold for higher-order structures of large molecular weight.

The dual mechanism of action strengthens the ability of the macrocyclic cavity-containing compounds to treat infections caused by Gram-negative bacteria by themselves. In addition, the dual mechanism of action strengthens the ability of the macrocyclic cavity-containing compounds to treat infections caused by Gram-negative bacteria with antibiotics, even those having intracellular targets. It was found that the macrocyclic cavity-containing compound and the antibiotic had a synergistic effect on an infection caused by a gram-negative bacterium. Without wishing to be bound by any theory, the dual mechanism of action of the macrocyclic cavity-containing molecule on Gram-negative bacteria forms the basis for the effective sensitization of a microbe towards an antimicrobial agent and thus leads to the reduction of the amount of an antimicrobial agent needed to prevent or inhibit the growth of the microbe in a subject or to kill the pathogenic microbe in a subject, when a macrocyclic cavity-containing compound and an antimicrobial agent are adminstered in combination.

In the present invention, both of the macrocyclic cavity-containing compound and the antimicrobial agent act as a biologically active ingredient. In one embodiment, the macrocyclic cavity-containing compound acts as a pharmaceutically active ingredient. In one embodiment, both of the macrocyclic cavity-containing compound and the antimicrobial agent act as pharmaceutically active ingredients. In one embodiment, the biological activity refers to pharmaceutical activity. In one embodiment, the biological activity refers to virulence suppressing activity. In one embodiment, both of the macrocyclic cavity-containing compound and the antimicrobial agent are used in antimicrobially effective an mounts. In one embodiment, the effect of the macrocyclic cavity-containing compound and the anti-bacterial agent is synergistic.

*Pseudomonas aeruginosa* is known to be one of the most problematic pathogenic micro-organisms. Indeed, in a laboratory environment, *P. aeruginosa* is resistant to nearly all antibiotics within a period of 3 to 4 days. Comparing the sequencing results of the bacterial RNA, with and without a pillarene[5]a (P[5]a, CAS No. 1351445-28-7), allowed the inventors to identify the processes that are affected by comparison with pre-determined gene set terms from the "KEGG pathway analysis" and the "GO Ontology" (see FIG. 1). These gene sets contain all the genes associated with a certain term, for instance "Biofilm", and the inventors referenced all the genes affected by P[5]a, to these gene sets. From this analysis (FIG. 1) it can be seen that a large amount of gene sets associated with virulence factors, including "Biofilm", "Quorum Sensing", "Bioverdine biosynthetic process" and "Biosynthesis of Secondary Metabolites" are downregulated by P[5]a.

Thus, P[5]a suppresses a large number of virulence factors that influence bacterial persistence and antibiotic accessibility (for instance, antibiotics are far less effective against bacteria that form a biofilm), but it also significantly downregulates bacterial antibiotic resistance genes. Some of the genes significantly down-regulated include "MexCD-OprJ", "MexAB-OprM" and "mexXY". These genes regulate membrane pumps, which can pump antibiotics out of the bacteria, and which are known to contribute significantly to multi-drug resistance in bacteria (Table. 1).

TABLE 1

Important resistance associated genes downregulated by P[5]a.

| Pump | Antibiotic Substrates | Role in virulence |
|---|---|---|
| MexCD-OprJ | β-lactams, Chloramphenicol, Fluoroquinolones, Novobiocin, Tetracycline | Host colonization, biofilm formation |
| MexAB-OprM | β-lactams, Chloramphenicol, Ethidium bromide, Fluoroquinolones, Macrolides, Quinolones, Tetracycline | Host colonization, invasion of host cells, quorum sensing |
| MexXY | Aminoglycosides, Macrolides, Tetracyclines | Colonization of cystic fibrosis lung, protection from oxidative damage |

Thus, a macrocyclic cavity-containing compound can reduce the amount of an antimicrobial agent required to kill pathogens. In addition, a macrocyclic cavity-containing compound can reduce the buildup of resistance from microbes to antimicrobial agents. According to the present invention, antimicrobial agents that encounter high resistance levels could become effective in treating and/or preventing microbial infections again, when administered with a macrocyclic cavity-containing compound.

In other words, according to the present invention a macrocyclic cavity-containing compound was found to make resistant bacteria susceptible to antimicrobial agents again in some instances. This is particularly useful for pan-drug resistant bacteria.

In the present invention, the macrocyclic cavity-containing compounds were found to function with a wide variety of antimicrobial agents/antibiotics. The macrocyclic cavity-containing compounds and anti-bacterial agents were found to have synergistic effects, such as a drop in minimal inhibitory concentrations and a significantly reduced resistance build-up of pathogens to the antibiotics. The effects were found with antimicrobial agents from a diverse range of classes and mechanisms. Examples of the antimicrobial agents are β-lactams such as penicillin derivatives, cephalosporins, carbepenems and β-lactamase inhibitors, aminoglycosides, fluoroquinolones, macrolides, tetracyclines, novobiosin, chloramphenicol, ethidium bromide and colistin.

In one embodiment, the antimicrobial agent is a β-lactam antibiotic or a combination of β-lactam antibiotics. In one embodiment, the β-lactam antibiotic is a penicillin derivative. In one embodiment, the penicillin derivative is piperacillin or ticarcillin. In one embodiment, the β-lactam antibiotic is a β-lactamase inhibitor. In one embodiment, the β-lactamase inhibitor is tazobactam or clavulanic acid. In one embodiment, the β-lactam antibiotic is a combination of a penicillin derivative and a β-lactamase inhibitor. In one embodiment the combination of a penicillin derivative and a β-lactamase inhibitor is a combination of pipercacillin and tazobactam or a combination of ticarcillin and clavulanic acid. In one embodiment, the combination of a β-lactamase inhibitor and a β-lactam antibiotic is a combination of imipenem and relebactam with cilastatin.

In one embodiment, the β-lactam antibiotic is a cephalosporin. In one embodiment, the cephalosporin is cefepime, ceftazidime, cefoperazone, cefpirome, ceftriaxone or ceftobiprole. In one embodiment, the β-lactam antibiotic is a carbepenem. In one embodiment, the carbepenem is imipenem, meropenem, ertapenem, doripenem, panipenem, biapenem or tebipenem.

In one embodiment, the antimicrobial agent is an aminoglycoside. In one embodiment, the aminoglycoside is kanamycin, amikacin, tobramycin, dibekacin, gentamycin, sismycin, netilmycin, neomycin B, neomycin C, neomycin E, streptomycin, or plazomycin. In one embodiment, the aminoglycoside is tobramycin.

In one embodiment, the antimicrobial agent is a fluoroquinolone. In one embodiment, the fluoroquinolone is ciprofloxacin, levofloxacin, garenoxacin, gatifloxacin, gemifloxacin, norfloxacin, ofloxacin or moxifloxacin. In one embodiment, the fluoroquinolone is levofloxacin.

In one embodiment, the antimicrobial agent is polymyxin. In one embodiment, the polymyxin is polymyxin B or colistin. In one embodiment, the polymyxin is colistin.

The present invention relates to use of a macrocyclic cavity-containing compound in sensitizing a microbe towards an antimicrobial agent and/or in sensitizing a microbe to become susceptible to an antimicrobial agent. The present invention relates also to the use of a macrocyclic cavity-containing compound in reducing the amount of an antimicrobial agent needed to prevent or inhibit the growth of a microbe in a subject. In addition, the present invention relates to the use of a macrocyclic cavity-containing compound in reducing the amount of an antimicrobial agent needed to kill a microbe in a subject. The invention relates also to use of a macrocyclic cavity-containing compound in prolonging the administration interval of an antimicrobial agent needed to induce bacteriostatic or bactericidal effects on a microbe in a subject. In addition, the present invention relates to the use of a macrocyclic cavity-containing compound in reducing the build-up of resistance of a microbe towards an antimicrobial agent. The present invention relates to use of a macrocyclic cavity-containing compound and an antimicrobial agent in inhibiting the growth of a microbe in a subject. The present invention relates also to use of a macrocyclic cavity-containing compound and an antimicrobial agent in inhibiting and/or treating and/or preventing a microbial infection in a subject having a microbial infection or being at risk of a microbial infection. The invention relates also to use of a macrocyclic cavity-containing compound and an antimicrobial agent in inhibiting and/or preventing the formation of biofilm by a microbe in a subject.

The present invention relates also to a macrocyclic cavity-containing compound and an antimicrobial agent for use in inhibiting and/or treating and/or preventing a microbial infection in subject having a microbial infection or being at risk of a microbial infection. Thus, the macrocyclic cavity-containing compound can be used as a preventive measure to reduce the risk of infections. In one embodiment, a macrocyclic cavity-containing compound and an antimicrobial agent are used in inhibiting and/or preventing a microbial infection in a subject being at risk of a microbial infection. Situations where subjects are at risk of a microbial infection include all types of invasive treatments and/or operations such as surgeries and implant installations, for example. Further, the invention relates also to a macrocyclic cavity-containing compound and an antimicrobial agent for use in inhibiting and/or preventing the formation of biofilm by a microbe in a subject. In one embodiment, the invention relates to a macrocyclic cavity-containing compound and an antimicrobial agent for use in treating a microbial infection in a subject by inhibiting and/or preventing the formation of biofilm by the microbe in the subject.

The present invention relates to a method of sensitizing a microbe towards an antimicrobial agent and/or in sensitizing a microbe to become susceptible to an antimicrobial agent by administrating a macrocyclic cavity-containing compound and an antimicrobial agent to a subject. The invention relates to a method of sensitizing a microbe towards an antimicrobial agent and/or in sensitizing a microbe to become susceptible to an antimicrobial agent by exposing the microbe to a macrocyclic cavity-containing compound and an antimicrobial agent. The present invention relates also to a method of reducing the build-up of resistance of a microbe towards an antimicrobial agent by exposing the microbe to a macrocyclic cavity-containing compound. In addition, the present invention relates to a method of reducing the amount of an antimicrobial agent needed to prevent or inhibit the growth of a microbe in a subject by administrating a macrocyclic cavity-containing compound and the antimicrobial agent to the subject. The present invention relates also to a method of reducing the amount of an antimicrobial agent needed to kill a microbe in a subject by administrating a macrocyclic cavity-containing compound and the antimicrobial agent to the subject. The present invention also relates to a method of prolonging the administration interval of an antimicrobial agent needed to induce bacteriostatic or bacteriocidal effect on a microbe by administrating a macrocyclic cavity-containing compound and the antimicrobial agent to the subject. The present invention relates to a method of inhibiting growth of a microbe in a subject by administering a macrocyclic cavity-containing compound and an antimicrobial agent to the subject. The present invention relates also to a method of inhibiting and/or treating and/or preventing a microbial infection in a subject having a microbial infection or being at risk of a microbial infection by administrating an antimicrobial agent, and a macrocyclic cavity-containing compound to the subject. In addition, the invention relates to a method of inhibiting, treating and/or preventing the formation of biofilm by a microbe in a subject by administrating a macrocyclic cavity-containing compound and an antimicrobial agent to the subject.

The present invention relates to a combined use of a macrocyclic cavity-containing compound and an antimicrobial agent to prevent and/or inhibit and/or treat a microbial infection in a subject. In one embodiment, the present invention relates to a composition or a dosage form or a kit comprising a macrocyclic cavity-containing compound and an antimicrobial agent. In one embodiment, the present invention relates to a composition or a dosage form or a kit comprising a macrocyclic cavity-containing compound for use before, during and/or after treatment with an antimicrobial agent.

In the present invention, the macrocyclic cavity-containing compound is able to bind to microbial signalling molecules or to microbial quorum sensing signal molecules. In one embodiment, the microbial signalling molecule or the microbial quorum sensing signal molecule is homoserine lactone (HSL) and/or N-acyl-homoserine lactone (AHL). The binding of the macrocyclic cavity-containing compound to microbial signalling molecules is strong and the compounds can absorb microbial signalling molecule concentrations even much higher than normally produced by natural bacteria. In the present invention, the macrocyclic cationic cavity-containing compound is also able to interact with extracellular DNA, which is a crucial component of the extrapolymeric substance, known to play a key role in early stage biofilm formation.

The macrocyclic cavity-containing compounds seem to have no negative growth effects on microbes. The absence of pressure has as a big advantage that it reduces the need for build-up of resistance to treatments. The host-guest binding of a macrocyclic cavity-containing compound and a microbial signalling molecule is solely an extracellular process. The macrocyclic cavity-containing compounds are too large to enter the microbial cells, which further reduces the chances of resistance development in microbes. The macrocyclic cavity-containing compounds seem to act as virulence inhibitors. The macrocyclic cavity-containing compound, such as a pillar[5]arene, has a very good stability and is easily dissolved, and even stable, in water. Thus, these compounds can be applied in a wide variety of environments. The macrocyclic cavity-containing compounds, such as cyclodextrins, cucurbit urils, pillar arenes, calix arenes, crown ethers and/or salts thereof, as well as their effects on microbial infections have been disclosed in detail in a co-pending patent application PCT/FI2019/050717, which is hereby incorporated by reference.

In one embodiment, the macrocyclic cavity-containing compound is selected from pillar arenes, calix arenes, crown ethers, cyclodextrins, cucurbit urils and/or salts thereof. In one embodiment, the macrocyclic cavity-containing compound is selected from pillararenes and/or salts thereof. In one embodiment, the macrocyclic cavity-containing compound is selected from pillar[5]arenes or salts thereof. In one embodiment, the pillar[5]arene is 4,9,14,19,24,26,28,30,32,34-Deca[2-(trimethylammonio)ethoxy]hexacyclo[21.2.2.$2^{3,6}.2^{8,11}.2^{13,16}.2^{18,21}$]pentatriacontal(25),3,5,8,10,13,15,18,20,23,26,28,30,32,34-pentadecaene•10bromide. In one embodiment, the macrocyclic cavity-containing compound is selected from crown ethers. In one embodiment, the crown ether is 18-crown-6 (1,4,7,10,13,16-Hexaoxacyclooctadecane). In one embodiment, the crown ether is 15-crown-5 (1,4,7,10,13-Pentaoxacyclopentadecane). In on embodiment, the macrocyclic cavity-containing compound is selected from cucurbit urils. In one embodiment, the cucurbit uril is cucurbit[6]uril. In one embodiment, the macrocyclic cavity-containing compound is selected from resorcin arenes and/or salts thereof. In one embodiment, the macrocyclic cavity-containing compound is resorcin[4]arene or a salt thereof. In one embodiment, the macrocyclic cavity-containing compound is selected from cyclodextrins or salts thereof. In one embodiment, the macrocyclic cavity-containing compound is selected from alpha-cyclodextrins, gamma-cyclodextrins or salts thereof. In one embodiment, the macrocyclic cavity-containing compound is alpha-cyclodextrin or a salt thereof. In one embodiment, the macrocyclic cavity-containing compound is gamma-cyclodextrin or a salt thereof. In one embodiment, the macrocyclic cavity-containing compound is selected from calixarenes or salts thereof. In one embodiment, the calixarene is 4-sulfocalix[4]arene.

In one embodiment, the macrocyclic cavity-containing compounds is selected from a group comprising a pillar[5]arene, a resorcin[4]arene, 18-crown-6, 15-crown-5, cucurbit[6]uril, an alpha-cyclodextrin, a gamma-cyclodextrin and 4-sulfocalix[4]arene.

In one embodiment, the macrocyclic cavity-containing compound is a pillararene or a salt thereof and the antibacterial agent is selected from the group consisting of β-lactams, cephalosporins, carbepenems and β-lactamase inhibitors, aminoglycosides, fluoroquinolones, macrolides, tetracyclines, novobiosin, chloramphenicol, ethidium bromide, colistin and a combination thereof. In one embodiment, the macrocyclic cavity-containing compound is a crown ether or a salt thereof and the antibacterial agent is selected from the group consisting of β-lactams, cephalosporins, carbepenems and β-lactamase inhibitors, aminoglycosides, fluoroquinolones, macrolides, tetracyclines, novobiosin, chloramphenicol, ethidium bromide, colistin and a combination thereof. In one embodiment, the macrocyclic cavity-containing compound is a cucurbit uril or a salt thereof and the antibacterial agent is selected from the group consisting of β-lactams, cephalosporins, carbepenems and β-lactamase inhibitors, aminoglycosides, fluoroquinolones, macrolides, tetracyclines, novobiosin, chloramphenicol, ethidium bromide, colistin and a combination thereof. In one embodiment, the macrocyclic cavity-containing compound is a cyclodextrin or a salt thereof and the antibacterial agent is selected from the group consisting of carbepenems and β-lactamase inhibitors, macrolides, novobiosin, chloramphenicol, ethidium bromide, colistin and a combination thereof. In one embodiment, the macrocyclic cavity-containing compound is a calixarene or a salt thereof and the antibacterial agent is selected from the group consisting of cephalosporins, carbepenems and β-lactamase inhibitors, macrolides, tetracyclines, novobiosin, chloramphenicol, ethidium bromide, colistin and a combination thereof.

In one embodiment, the macrocyclic cavity-containing compound is a pillararene and the antimicrobial agent is colistin. In one embodiment, the macrocyclic cavity-containing compound is a pillararene and the antimicrobial agent is a fluoroquinolone, such as levofloxacin. In one embodiment, the macrocyclic cavity-containing compound is pillararene, such as pillar[5]arene and the fluoroquinoline is ciprofloxacin. In one embodiment, the macrocyclic cavity-containing compound is a pillararene and the antimicrobial agent is a β-lactam antibiotic, such as cephalosporin. In one embodiment, the pillararene is pillar[5]arene and the β-lactam antibiotic is cephalosporin. In one embodiment, the pillararene is pillar[5]arene and the β-lactam antibiotic is cefepime. In one embodiment, the macrocyclic cavity-containing compound is a pillararene, such as pillar[5]arene and the antimicrobial agent is a β-lactam antibiotic, such as aztreonam. In one embodiment, the macrocyclic cavity-containing compound is a pillararene, such as pillar[5]arene, and the anti antimicrobial agent is an aminoglycoside, such as tobramycin. In one embodiment, the macrocyclic cavity-containing compound is a pillararene, such as pillar[5]arene, and the antimicrobial agent is meropenem. In one embodiment, the macrocyclic cavity-containing compound is a pillararene, such as pillar[5]arene, and the antimicrobial agent is a macrolide, such as azithromycin.

In one embodiment, the macrocyclic cavity-containing compound is a crown ether and the antimicrobial agent is a polymyxin. In one embodiment, the crown ether is 18-crown-6 and the polymyxin is colistin. In one embodiment, the macrocyclic cavity-containing compound is a crown ether and the antimicrobial agent is an aminoglycoside. In one embodiment, the crown ether is 15-crown-5 and the aminoglycoside is amikacin.

In one embodiment, the macrocyclic cavity-containing compound is a cyclodextrin and the antimicrobial agent is a fluoroquinolone. In one embodiment, the cyclodextrin is γ-cyclodextrin and the fluoroquinoline is ciprofloxacin. In one embodiment, the macrocyclic cavity-containing compound is a cyclodextrin and the antimicrobial agent is colistin. In one embodiment, the macrocyclic cavity-containing compound is a cyclodextrin and the antimicrobial agent is a fluoroquinolone, such as levofloxacin. In one embodiment, the macrocyclic cavity-containing compound is cyclodextrin and the fluoroquinoline is ciprofloxacin. In one embodiment, the macrocyclic cavity-containing compound is a cyclodextrin and the antimicrobial agent is a β-lactam antibiotic, such as aztreonam. In one embodiment, the macrocyclic cavity-containing compound is a cyclodextrin and the anti antimicrobial agent is an aminoglycoside, such as tobramycin. In one embodiment, the macrocyclic cavity-containing compound is a cyclodextrin and the antimicrobial agent is a macrolide, such as azithromycin. In one embodiment, the microbe is a bacterium or the microbial infection is caused by bacteria. In one embodiment, the microbe is or the microbial infection is caused by a bacterium that is resistant against the major antimicrobial agents typically used in the treatment of the infections caused by said bacterium. In one embodiment, the microbe is or the microbial infection is caused by a bacterium that has developed multiple drug resistance to broad-spectrum antibiotics. In one embodiment, the microbe belongs to or the microbial infection is caused by Gram-positive bacteria. In one embodiment, the microbe belongs to or the microbial infection is caused by bacteria belonging to genera *Staphylococcus*. In one embodiment, the microbe is or the microbial infection is caused by *Staphylococcus aureus*. In one embodiment, the microbe belongs to or the microbial infection is caused by Gram-negative bacteria. In one embodiment, the microbe belongs to or the microbial infection is caused by bacteria belonging to genera *Pseudomonas, Acinetobacter, Vibrio, Enterobacter, Escherichia, Kluyvera, Salmonella, Shigella, Helicobacter, Haemophilus, Proteus, Serratia, Moraxella, Stenotrophomonas*, Bdellovibrio, Campylobacter, *Yersinia, Morganella, Neisseria, Rhizobium, Legionella, Klebsiella, Citrobacter, Cronobacter, Ralstonia, Xylella, Xanthomonas, Erwinia*, Agrobacterium, *Burkholderia, Pectobacterium, Pantoea*, Acidovorax or any other genus of the family Enterobacteriaceae. In one embodiment, the microbe belongs to or the microbial infection is caused by bacteria belonging to genera *Pseudomonas*. In one embodiment, the microbe belongs to or the microbial infection is caused by bacteria belonging to genera *Acinetobacter*. In one embodiment, the microbe belongs to or the microbial infection is caused by bacteria belonging to genera *Vibrio*. In one embodiment, the microbe belongs to or the microbial infection is caused by bacteria belonging to genera *Yersinia*. In one embodiment, the microbe belongs to or the microbial infection is caused by bacteria belonging to genera

*Rhizobium*. In one embodiment, the microbe belongs to or the microbial infection is caused by bacteria belonging to genera *Klebsiella*. In one embodiment, the microbe is or the microbial infection is caused by *Pseudomonas aeruginosa, Acinetobacter baumannii, Vibrio cholera, Vibrio fischeri, Yersinia pestis, Rhizobium leguminosarum* or *Klebsiella pneumoniae*. In one embodiment, the microbe is or the microbial infection is caused by *Pseudomonas aeruginosa*. In one embodiment, the microbe is or the microbial infection is caused by *Acinetobacter baumannii*. In one embodiment, the microbe is or the microbial infection is caused by *Vibrio cholera*. In one embodiment, the microbe is or the microbial infection is caused by *Vibrio fischeri*. In one embodiment, the microbe is or the microbial infection is caused by *Yersinia pestis*. In one embodiment, the microbe is or the microbial infection is caused by *Rhizobium* leguminosarum. In one embodiment, the microbe is or the microbial infection is caused by *Klebsiella pneumoniae*. The present invention involves a dual mechanism of action of a macrocyclic cavity-containing compound on a Gram-negative microorganism, wherein the compound attenuates the virulence through binding of a microbial signaling molecule inside the inner cavity of the compound molecule and sensitizes the bacterial outer membrane by its positively charged functional side groups.

The microbial infection can be a local infection or a systemic infection. In one embodiment, the microbial infection is a local infection. In one embodiment, the microbial infection is a pulmonary infection. In one embodiment, the microbial infection is a systemic infection. In one embodiment, the microbial infection relates to a disease or a disorder that increases risk of microbial infection in a subject. In one embodiment, the microbial infection relates to cystic fibrosis.

In one embodiment, the subject is a human or an animal. In one embodiment, the subject is a plant. In one embodiment, the subject is a cell culture. In one embodiment, the subject is a non-living object. In one embodiment, the non-living object is a surface or a coating. In one embodiment, the non-living object is a medical device, an implant or a prosthesis. In one embodiment, the non-living object is an aqueous medium.

In the present invention, the macrocyclic cavity-containing compound acts as a biologically active ingredient. In one embodiment, the macrocyclic cavity-containing compound acts as a pharmaceutically active ingredient. In one embodiment, the biological activity refers to virulence suppressing activity.

The macrocyclic cavity-containing compound can be used and/or administered to a subject before, during and/or after a treatment with an antimicrobial agent. In one embodiment, the macrocyclic cavity-containing compound is added to an existing treatment with an antimicrobial agent. In one embodiment, an antimicrobial agent and a macrocyclic cavity-containing compound are administered to a subject simultaneously. In one embodiment, an antimicrobial agent and a macrocyclic cavity-containing compound are administered to a subject sequentially. In one embodiment, a macrocyclic cavity-containing compound is administered to a subject as a pretreatment, which is followed by administration of an antimicrobial agent. In one embodiment, an antimicrobial agent is first administered to a subject, followed by administration of a macrocyclic cavity-containing compound. In one embodiment, an antimicrobial agent and a macrocyclic cavity-containing compound are administered to a subject as a course of several treatments and/or dosages. In one embodiment, an antimicrobial agent and a macrocyclic cavity-containing compound are administered to a subject once a day. In one embodiment, an antimicrobial agent and a macrocyclic cavity-containing compound are administered to a subject once a day during several (7 to 14) days. In one embodiment, an antimicrobial agent and a macrocyclic cavity-containing compound are administered to a subject several times (2 to 4) a day. In one embodiment, an antimicrobial agent and a macrocyclic cavity-containing compound are administered to a subject several times (2-4) a day during several (7 to 15) days.

In one embodiment, the invention relates to a composition comprising at least one macrocyclic cavity-containing compound, an antimicrobial agent and optionally an acceptable carrier. In one embodiment, the invention relates to a kit comprising at least one macrocyclic cavity-containing compound and an antimicrobial agent. In one embodiment, the composition is a pharmaceutical composition. In one embodiment, the kit is a pharmaceutical kit. In one embodiment, the invention relates to a pharmaceutical composition comprising a macrocyclic cavity-containing compound, an antimicrobial agent and a pharmaceutically acceptable carrier for inhibiting/treating/preventing a microbial infection in a subject. The composition of the present invention can be prepared by techniques known in the art. The composition can thus be in liquid, solid or powder form, for example. The pharmaceutical composition of the present invention can be administered orally, parenterally, topically or by inhalation, for example. In one embodiment, the pharmaceutical composition is in the form of microparticles. In one embodiment, the microparticles are in the range of 1-5 μm. Depending on its route of administration, the composition contains necessary pharmaceutically acceptable additives and/or ingredients, such as fillers, diluents and/or adjuvants.

In one embodiment, the microbial infection is a chronic infection. In one embodiment, the infection is an acute infection or the infection is caused by planktonic microbes.

The following examples are given to further illustrate the invention without, however, restricting the invention thereto.

EXAMPLES

Example 1

The downregulation of many virulence factors and antibiotic resistance genes when treated with P[5]a, suggests that the effects of macrocyclic cavity containing compounds might make antibiotics more effective against bacteria again. Because of this, a combined administration of P[5]a with a variety of antibiotics was tested. MIC values with two different antibiotics, meropenem and cefepime (FIG. 2) were tested, over a period of 14 consecutive days (which more than surpasses the length of normal treatments, 7-10 days), when administered together with and without 2.5 mM P[5]a.

It was found that the buildup of resistance by a pathogenic Gram-negative bacterium *Pseudomonas aeruginosa* strain PAO1 to these 2 different classes was significantly reduced over time when P[5]a is added. Thus, targeting separately the virulence factors of these bacteria and antibiotic resistance genes can also have major effects on the potency of antibiotics. Two major benefits include 1) less antibiotic is required to kill the bacterium and 2) the overall global rise of resistance in bacteria against antibiotics, could be significantly reduced. Interestingly, P[5]a functions also well with the carbepenem antibiotic meropenem. This class of antibiotics is often seen as the last line of defense against resistant bacteria.

Figure 2:
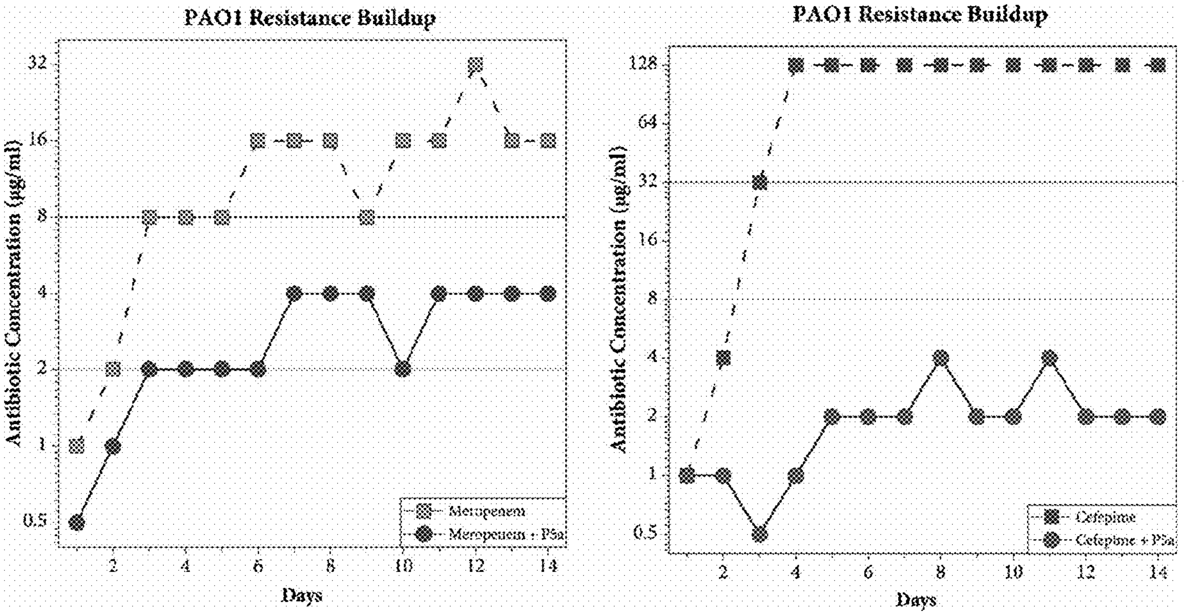
FIG. 2 shows the antibiotic resistance buildup of *P. aeruginosa* PAO1 to cefepime (cephem antibiotic class) and to meropenem (carbepenem antibiotic class). Area below the yellow line means that the bacterium is classified as susceptible to the antibiotic. The area in between yellow and red means that the bacterium is intermediate susceptible to the antibiotic. The area above the red line means that the bacterium is classified as resistant to the antibiotic (According to the "Performance Standards for Antimicrobial Susceptibility Testing", which is maintained by the Clinical and Laboratory Standards Institute).
Figure 3:
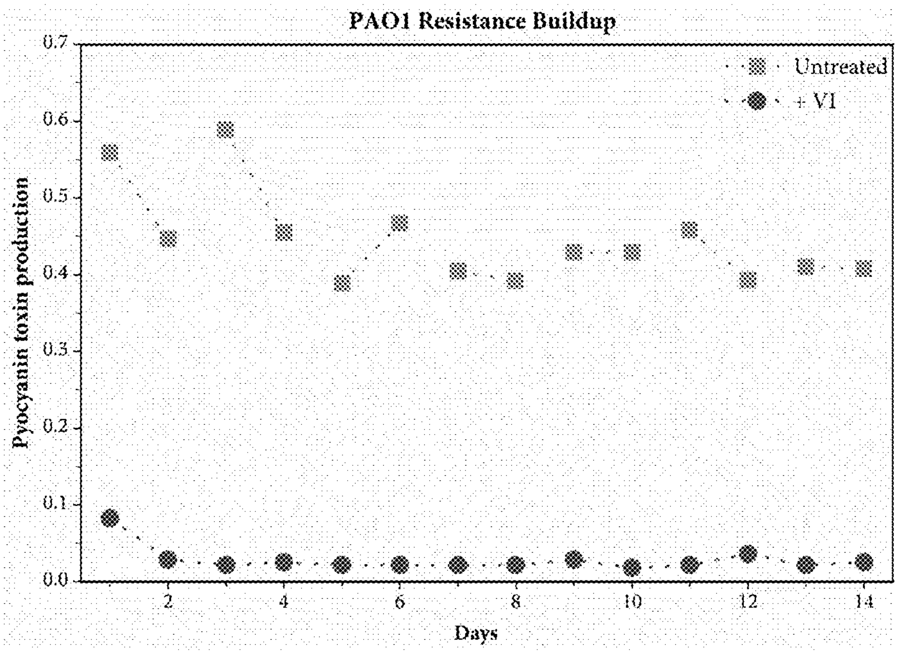
FIG. 3 shows the results of the pyocyanin toxin production by *P. aeruginosa* PAO1, followed over a period of 14 days. Throughout the 14 days period, P5a was very efficient in suppressing the toxin formation, while no decrease in bacterial viability was detectable.

In this experiment, the minimum inhibitory concentration MIC was analyzed daily for 14 consecutive days, and the highest MIC values (so the highest concentration of antibiotic where the bacteria still grew) was used for the next day. This way, the buildup of resistance over time can be monitored. In FIG. 2, the area below the yellow line means that the bacterium is classified as susceptible to the antibiotic, the area in between yellow and red means that the bacterium is intermediate susceptible to the antibiotic and the area above the red line means that the bacterium is classified as resistant to the antibiotic (According to the "Performance Standards for Antimicrobial Susceptibility Testing", which is maintained by the Clinical and Laboratory Standards Institute).

Example 2

Since the RNA sequencing revealed that the P[5]a treatment downregulates genes associated with widespread multidrug resistance, the inventors proposed that P[5]a might also increase the effectivity of a wide variety of types of antibiotics (rather than a single specific mechanism, like for instance β-lactam inhibitors). So, it was tested whether P[5]a could sensitize (increase the efficacy of) already resistant *P. aeruginosa* strains PA 5834 (FIG. 4) and PA 5539 (FIG. 5), that are resistant to a wide variety of antibiotics. To test this, two MDR *P. aeruginosa* strains from clinical isolates were used. These isolates were obtained from patients in the Meilahti hospital (Helsinki, Finland). The antibiotics used, and their different mechanisms of actions, are described in Table 2.

TABLE 2

Antibiotics used in the sensitizing effect test.

| Name | Short Name | Class | Mechanism | Test Group |
|---|---|---|---|---|
| Amikacin | AMK | Aminoglycoside | Protein synthesis, 16S | B |
| Cefepime | CPM | Cephem | Protein synthesis | B |
| Ceftazidime | CAZ | Cephem | Cell wall synthesis | A |
| Colistin | CL | Lipopeptide | Cell Membrane | O |
| Ceftriaxone | CTR | Cephem | Cell wall synthesis | B |
| Imipenem | IPM | Carbepenem | Cell wall synthesis | B |
| Levofloxacin | LVFX | Fluoroquinolone | DNA gyrase | B |
| Meropenem | MEM | Carbepenem | Cell wall synthesis | B |

Figure 4:
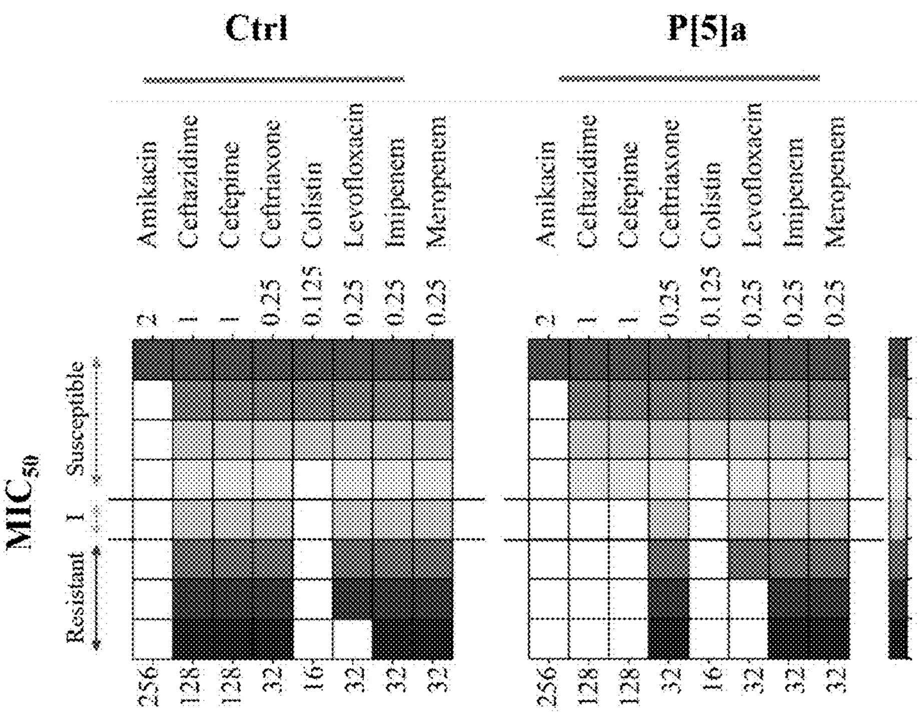
FIG. 4 shows the minimum inhibitory concentrations (MIC) of a selection of antibiotics on a multidrug resistant *P. aeruginosa* strain PA 5834 when administered without and with P[5]a, in Luria broth medium. Values in blue, yellow and orange indicate the bacterium is categorized as "susceptible", "intermediate susceptible" and "resistant", respectively, according to the "Performance Standards for Antimicrobial Susceptibility Testing", which is maintained by the Clinical and Laboratory Standards Institute.
Figure 5:
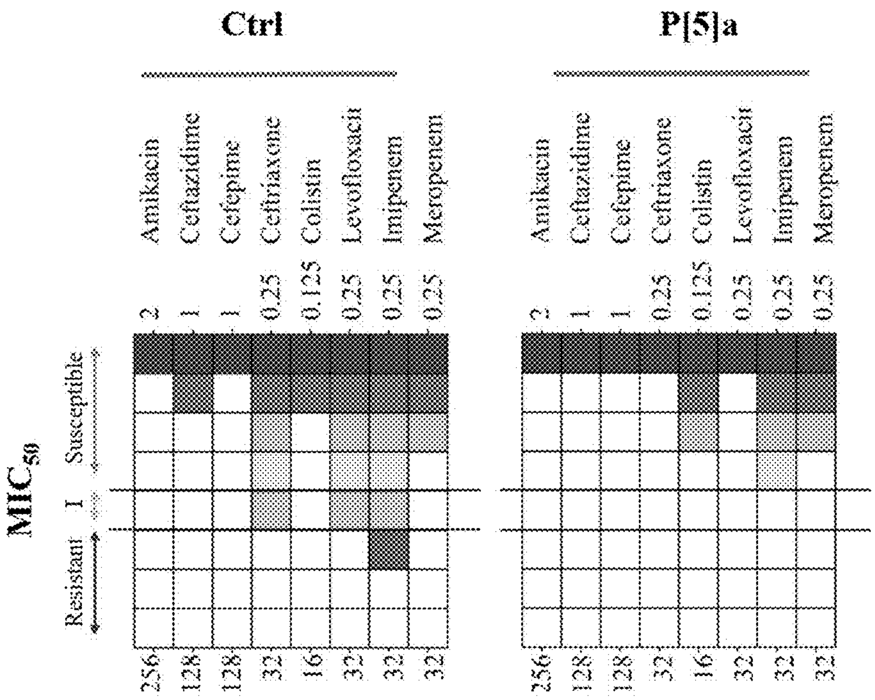
FIG. 5 shows the minimum inhibitory concentrations (MIC) of a selection of antibiotics on a multidrug resistant *P. aeruginosa* strain PA 5539 when administered without and with P[5]a, in Luria broth medium. Values in blue, yellow and orange indicate the bacterium is categorized as "susceptible", "intermediate susceptible" and "resistant", respectively, according to the "Performance Standards for Antimicrobial Susceptibility Testing", which is maintained by the Clinical and Laboratory Standards Institute.
Figure 6:
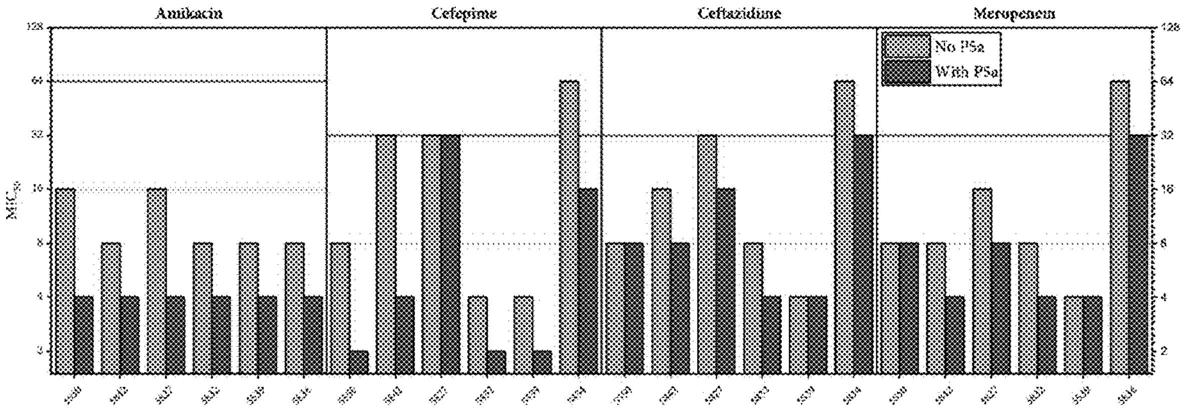
FIG. 6 shows the minimum inhibitory concentrations (MIC) of amikacin, cefepime, ceftazidime and meropenem on resistant *P. aeruginosa* strains PA 5550, PA 5842, PA 5827, PA 5832, PA 5834 and PA 5539 in the presence or absence of P[5]a, in Mueller broth medium.

It shows that P[5]a functions as a sensitizer with all tested antibiotics and has the synergistic effect with a variety of antibiotics. In FIG. 4 with *P. aeruginosa* strain PA 5834, P[5]a made the bacterium classify as "susceptible" again, whereas without P[5]a it was fully "resistant" to the antibiotics ceftazidime and cefepime (even growing in the highest concentration we tested). This could have major implications, because there have been many encounters already of "Pan-Drug resistant bacteria" bacteria that are classified as "resistant" to all known antibiotics. They are basically untreatable by current standards. P[5]a Virulence inhibitors, might make those bacteria susceptible again for treatment. In FIG. 5 with *P. aeruginosa* strain PA 5539, the overall resistance profile of the bacterium was much lower. There the sensitizing effect could be seen with nearly all antibiotics. Further testing was done on six resistant *P. aeruginosa* strains from the Helsinki hospital collection, PA 5550, PA 5842, PA 5827, PA 5832, PA 5834 and PA 5539 with four different antibiotics (amikacin, cefepime, ceftazidime and meropenem). In all cases the sensitizing effects were observed. The results are shown in FIG. 6.

Example 3—Biofilm Formation

The effect of P[5]a on the formation of biofilm by a pathogenic Gram-negative bacterium, *Pseudomonas aeruginosa*, strain PA01 was measured.

Figure 7:
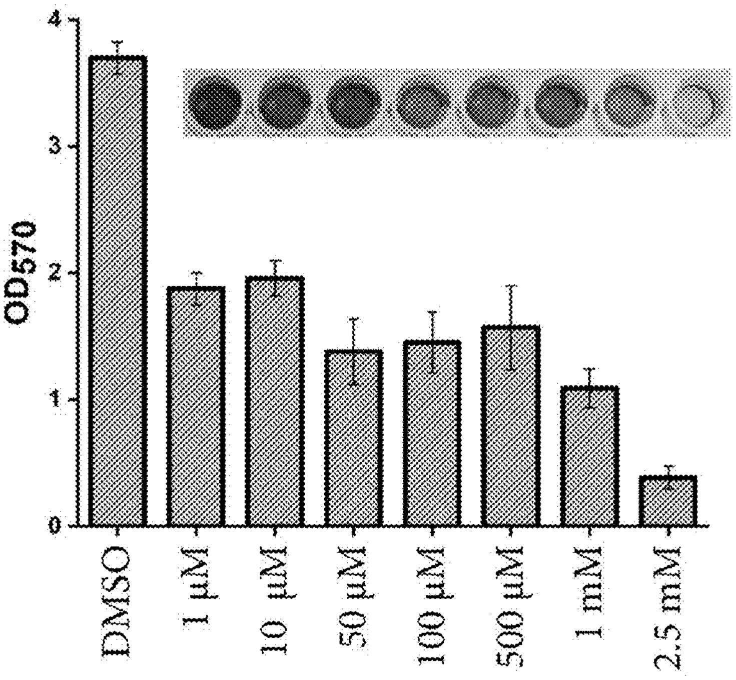
FIG. 7 shows the effect of P[5]a on the formation of biofilms by a pathogenic Gram-negative bacterium, *Pseudomonas aeruginosa*, strain PA01 (Example 3).
Figure 8:
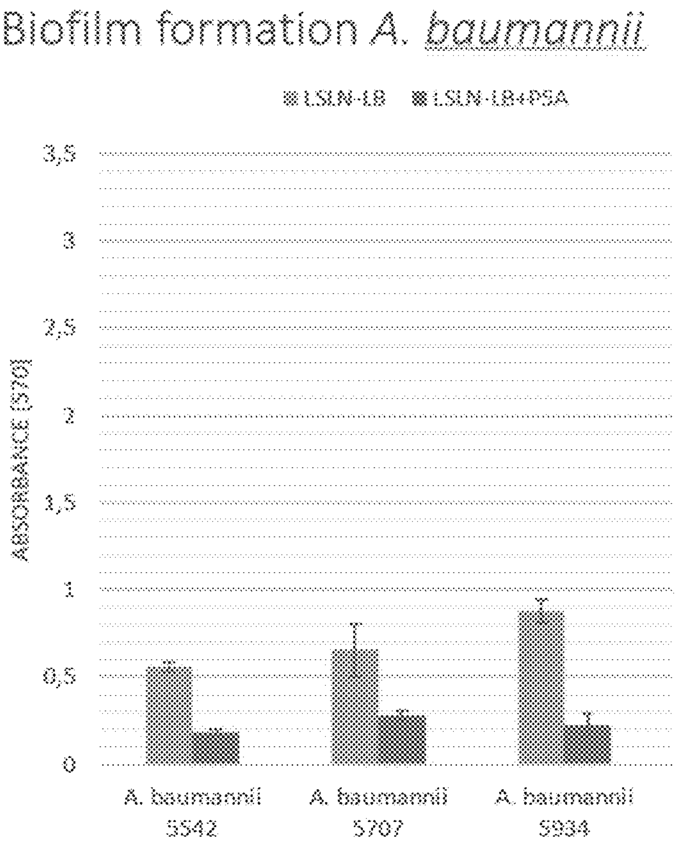
FIG. 8 shows the effect of P[5]a on the formation of biofilms by 3 strains of the pathogenic Gram-negative bacteria, *Acinetobacter baumannii.*

P[5]a in high concentrations significantly reduced the biofilm formation. The results are shown in FIG. 7. Biofilm is, alongside pyocyanin production, an important indicator of virulence in *P. aeruginosa*. The inhibition of biofilm, might also make antibiotics more effective, because antibiotics do not efficiently penetrate biofilms and as such bacteria within the biofilm are tolerant to very high concentrations of antibiotic.

Example 4

Figure 9:
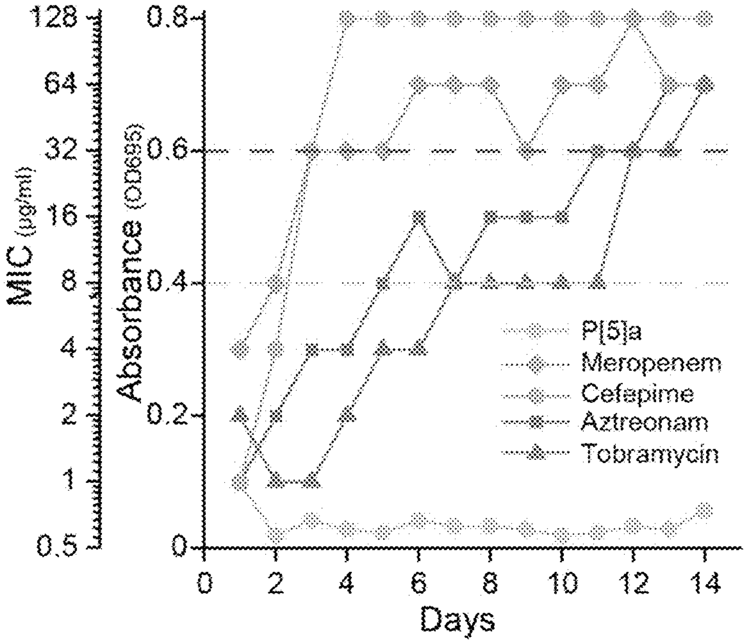
FIG. 9 shows that P[5]a does not encounter resistance development over 14-day period in a pathogenic Gram-negative bacterium, *P. aeruginosa*, strain PA01 (Example 4).

The effect of P[5]a on encountering resistance development in a pathogenic Gram-negative bacterium, *Pseudomonas aeruginosa*, strain PA01 was studied over 14-day period. The development of resistance over 14 continuous days by the pathogen PAO1 towards treatment with four clinically relevant antibiotics (meropenem, cefepime, aztreonam and tobramycin) and P[5]a was compared. For the antibiotics, MICs were monitored in accordance with CLSI guidelines (Testing, S. Clinical and Laboratory Standards Institute: Performance Standards for Antimicrobial Susceptibility Testing Supplement M100S. 2016), whereas with P[5]a the toxin inhibition was monitored since it lacks direct antimicrobial properties. P[5]a successfully suppressed toxin levels throughout the 14 days, with no observable decrease of effectivity. In all antibiotic treatments, reduced susceptibility was observed from day 4 onwards, with complete resistance to all treatments after 12 days. The results are shown in FIG. 9.

Example 5

Figure 10:
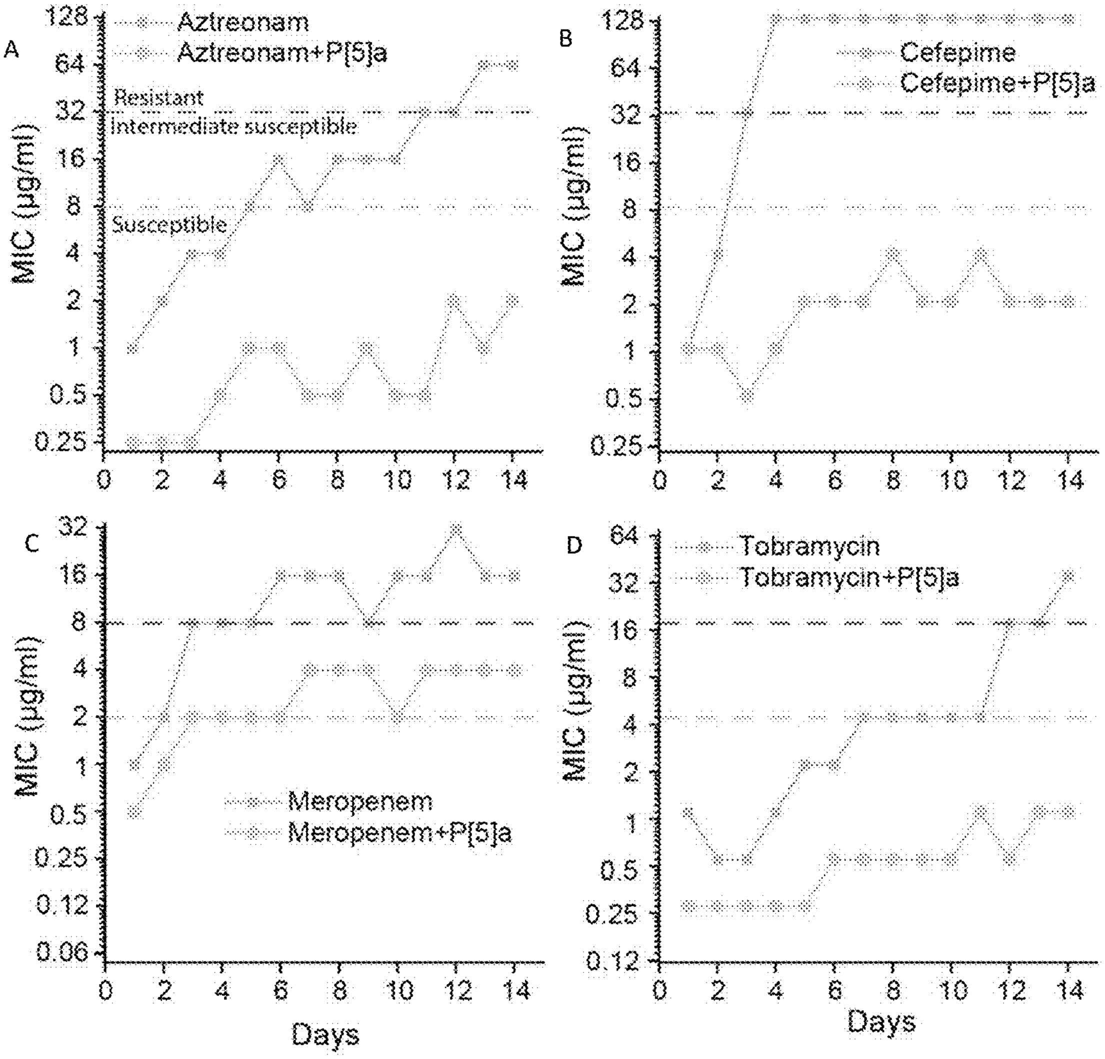
FIG. 10 shows the effect of P[5]a on the enhancement of the penetration of coadministered antibiotics aztreonam (A), cefepime (B), meropenem (C) and tobramycin (D). The upper dashed line (the red one) indicates the resistance level. The lower dashed line (the yellow one) indicates the susceptibility level. The area between the dashed lines indicates intermediate susceptibility (Example 5).
Figure 11:
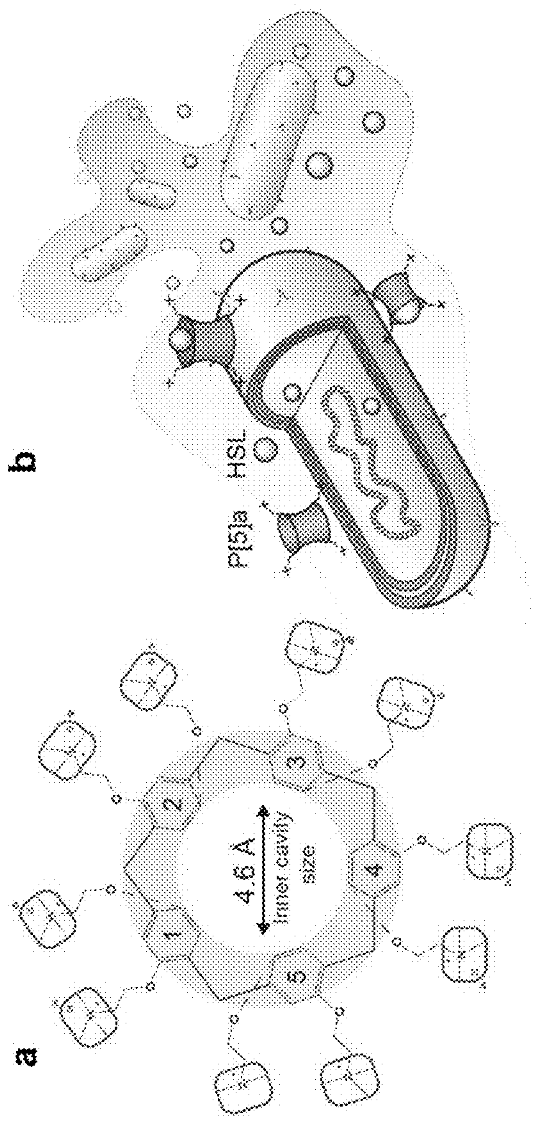
FIG. 11 shows a schematic representation of the structural features that lead to a dual mechanism of action of P[5]a. a) Highlighted in orange is the hydrophobic core of the structure, with a cavity size of 4.6 Å, which binds the signalling molecule. Highlighted in blue are the positively charged amino groups that interact with the negatively charged surface of the cell membrane. b) Graphic representation of the effects of the proposed dual mechanisms of P[5]a on *P. aeruginosa.*

The effect of P[5]a on the enhancement of the penetration of coadministered antibiotics having intracellular targets (aztreonam, cefepime, meropenem and tobramycin) was studied over 14-day period in a pathogenic Gram-negative bacterium, *Pseudomonas aeruginosa*, strain PA01. The coadministration of P[5]a with the antibiotics aztreonam (a), cefepime (b), meropenem (c) and tobramycin (d) greatly slowed the development of resistance by the pathogen to the respective antibiotic treatment. MIC values were categorized in three groups according to the Clinical and Laboratory Standards Institute: susceptible, intermediate susceptible and resistant. Cefepime reached 128 μg/ml after four days, which was the highest concentration of antibiotic included. The results are shown in FIG. 10.

Example 6

The interaction of P[5]a with lipopolysaccharides of *P. aeruginosa*, strain PA10 was measured using AUC. The results are shown in FIG. 12.

Analytical ultracentrifugation (AUC) is based on sedimentation of colloidal particles in a centrifugal field. During centrifugation particles move toward the bottom of the measuring cell. This movement leads to redistribution of particles along the measuring cell, which in turn can be expressed as a change in concentration along the measuring cell. The absorbance detector was used to follow the changes caused by centrifugation (absorbance is proportional to concentration). In simple words, in AUC the inventors measure how concentration changes during centrifugation, so they collect concentration profiles. Interaction between particles can be measured as a result of changes in the sedimentation profiles. In sedimentation velocity one uses high speed and collect the data (concentration profiles) during sedimentation process at different time points (many profiles).

The spectra of both P[5]a and LPS from *P. aeruginosa* were first analysed separately (see FIGS. 12 *a* and *b*). At 305 nm, P[5]a displays a clear and steady sedimentation profile over time (as indicated by the Y-axis radius). At 305 nm, LPS does not display a sedimentation profile. Because only the sedimentation of P[5]a was detected at 305 nm, the inventors were certain that any changes observed in the sedimentation profile, come from interactions between P[5]a and other particles. The inventors then combined P[5]a together with LPS. LPS varies in composition and has a molecular weight range between 10-20 kDa (see FIG. 12 *c*). Rapid sedimentation of some particles were observed. Analysis of the molecular weight of the particles shows a large distribution of sizes (see FIG. 12 *d*). The inventors observed a big first peak at low molecular weight (and a steady sedimentation spectrum in FIG. 12 *c*, which is reminiscent of unbound P[5]a in FIG. 12 *a*). This represents unbound P[5]a, meaning there was a large excess of unbound particles. The inventors also observed lower peaks across a large range of molecular weights. This indicates that P[5]a is capable of interacting with multiple LPS particles, to form polydisperse structures.

sigmaaldrich.com/catalog/product/sigma/19143?lang=fi&region=FI

Example 7

To measure the binding affinity between the macrocyclic "Host" P[5]a and different homoserine lactone "guests" a competitive-binding assay was used. In this case, a "guest" HSL solution is titrated against a solution of the P[5]a "host", which has a fluorescent dye bound in its cavity, Methylene Orange, which has a known affinity for the P[5]a. The ratio of P[5]a to HSL enables calculation of the affinity.

Figure 13:
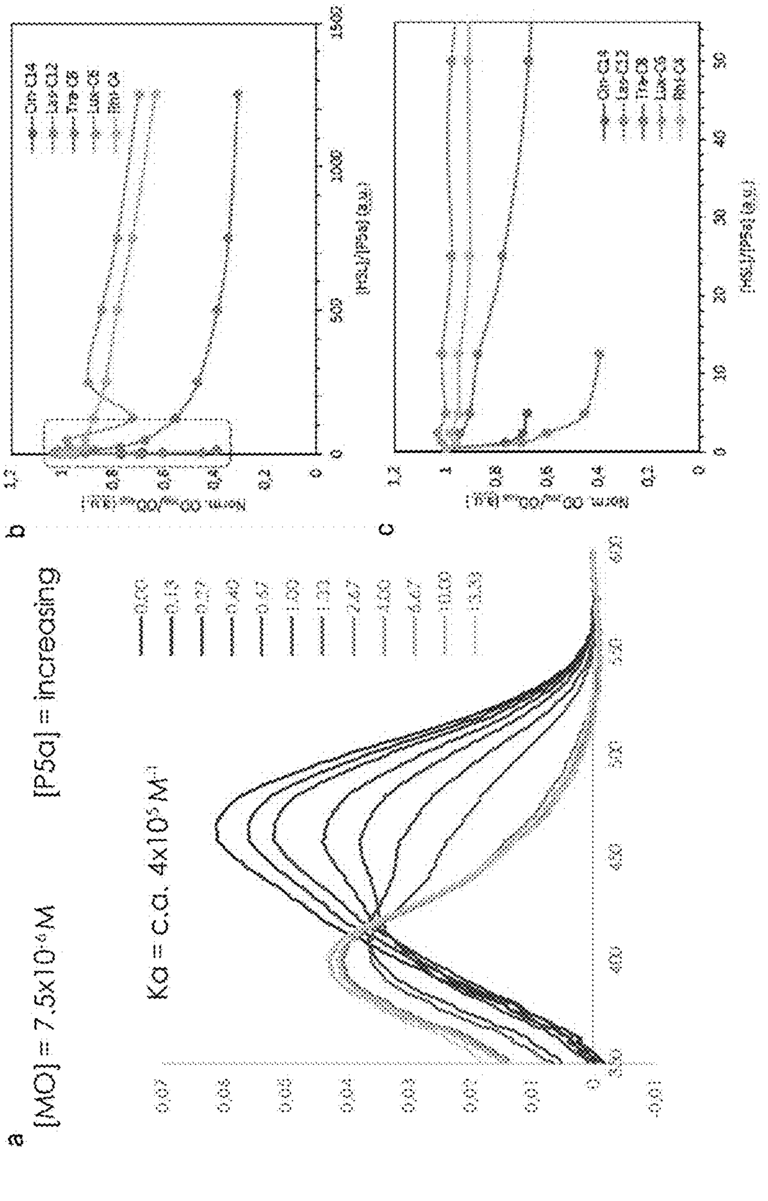
FIG. 13 shows binding affinity measurements between P[5]a host and HSL guests using dye displacement assays. The results show clear preference for HSLs with a long carbon moiety. a, Principle of Guest displacement assay (GDA), where the host P[5]a binds a host inside its cavity, leading to a shift in the fluorescence spectrum from 468 to 398 nm. The addition of a HSL "guest" displaces the guest from the cavity again, resulting in a shift back to 468 nm. The concentrations at which this displacement happens, can be used to calculate the affinity. b, The affinity of five different HSLs were measured, the 3-OH—C14 (Cin) HSL, the 3-Oxo-C12 (Las) HSL, the 3-Oxo-C8 (Tra) HSL, the 3-Oxo-C6 (Lux) HSL and the C4 (Rhl) HSL, and it was plotted against the HSL/P[5]a ratio. c, Zoom in (as indicated by the dashed line from FIG. 13*b*) shows high binding affinity for the 3-OH—C14 HSL and 3-Oxo-C12 HSL (Example 7).

A strong displacement (i.e. high binding affinity) with the long carbon moieties 3-OH—C14 HSL and 3-Oxo-C12 HSL was observed. Medium displacement was observed with the 3-Oxo-C8 HSL. Poor displacement was observed with both the 3-Oxo-C6 and C4 HSLs. The results are shown in FIG. 13.

Example 8

Figure 14:
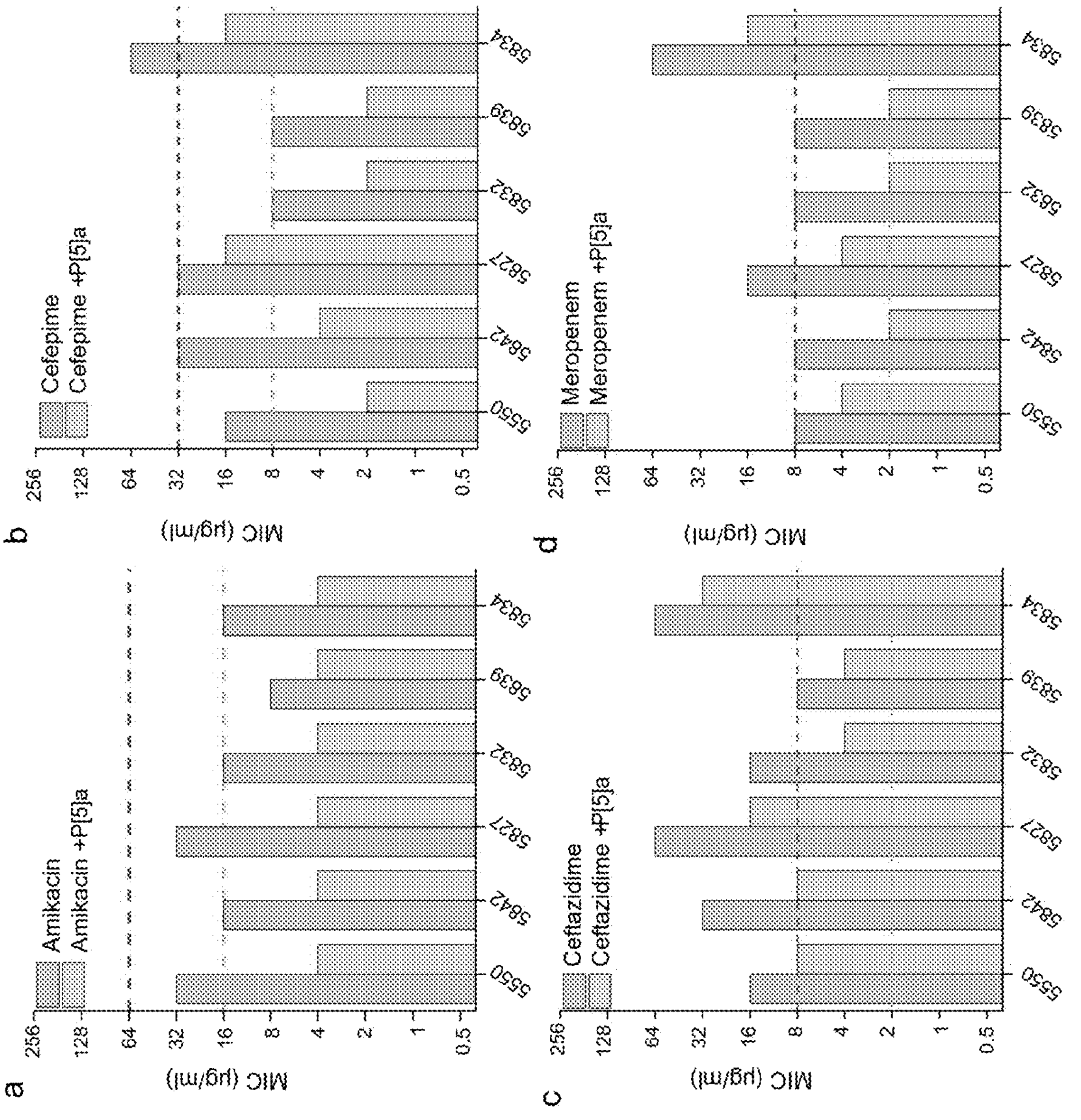
FIG. 14 shows how P[5]a enhances the penetration and efficacy of coadministered antibiotics Amikacin (a), Cefepime (b), Ceftazidime (c) and Meropenem (d) in MDR resistant clinical isolates (Example 8).

The effect of P[5]a on the penetration and efficacy of coadministered antibiotics Amikacin (a), Cefepime (b), Ceftazidime (c) and Meropenem (d) in MDR resistant clinical isolates were studied. The resistance profiles and detailed strain information are provided in Table 3 below. The results are shown in FIG. 14.

TABLE 3

| code | Species | Further specification | Antibiotic resistance |
|---|---|---|---|
| 5542 | MDR-*Acinetobacter baumannii* | | Resistant to Amikacin, Amoxicillin-clavulanate, Ampicillin, Azithromycin, Cefalexin, Ertapenem, Levofloxacin, Meropenem, Minocycline, Piperacillin-tazobactam, Tigecycline, Tobramycin and Sulfamethoxazole |
| 5707 | MDR-*Acinetobacter baumannii* | | MDR |
| 5934 | MDR-*Acinetobacter baumannii* | | MDR |
| IATSO18 | *Pseudomonas aeruginosa* | ATCC 33365 | |
| IATSO12 | *Pseudomonas aeruginosa* | ATCC 33359 | |
| IATSO11 | *Pseudomonas aeruginosa* | ATCC 33358 | |
| IATSO10 | *Pseudomonas aeruginosa* | ATCC 33357 | |
| IATSO9 | *Pseudomonas aeruginosa* | ATCC 33356 | |
| IATSO8 | *Pseudomonas aeruginosa* | ATCC 33355 | |
| IATSO5 (PA01) | *Pseudomonas aeruginosa* | ATCC 33352 | |
| IATSO3 | *Pseudomonas aeruginosa* | ATCC 33350 | |
| IATSO1 | *Pseudomonas aeruginosa* | ATCC 33348 | |
| 5542 | *Pseudomonas aeruginosa* | | MDR intermediate susceptible to amikacin 16 ug, resistant to cefepime 32 ug, ceftazidime 32 ug and meropenem 8 ug |
| 5834 | *Pseudomonas aeruginosa* | | MDR intermediate susceptible to amikacin 16 ug, resistant to cefepime 64 ug, ceftazidime 64 ug and meropenem 64 ug |
| 5832 | *Pseudomonas aeruginosa* | | MDR Intermediate susceptible to amikacin 16 ug and to cefepime 8 ug, resistant to ceftazidime16 ug and meropenem 8 ug, resistant to ciprofloxacin |
| 5827 | *Pseudomonas aeruginosa* | | MDR Intermediate susceptible to amikacin 32 ug, resistant to cefepime 32 ug, ceftazidime 64 ug and meropenem 16 ug |
| 5550 | *Pseudomonas aeruginosa* | | MDR Intermediate susceptible to amikacin 32 ug and to cefepime 16 ug, resistant to ceftazidime 16 ug and meropenem 8 ug |
| 5539 | *Pseudomonas aeruginosa* | | Susceptible to Amikacin 8 ug, intermediate to Cefepime 8 ug, resistant to ceftazidime 8 ug and meropenem 8 ug and imipenem, cefurixome, pipiracillin-tazobactam, ciprofloxacin and tobramycin |

TABLE 3-continued

| code | Species | Further specification | Antibiotic resistance |
|---|---|---|---|
| 2798 | *Pseudomonas aeruginosa* | ATCC 2798 | Susceptible to Amikacin & Colistin, Intermediate susceptible to Aztreonam & Cefepime, Resistant to Ceftazidime, Cirpofloxacin, Doripenem, Imipenem, Meropenem, Levofloxacin & Piperacillin-tazobactam |

It will be obvious to a person skilled in the art that, as the technology advances, the inventive concept can be implemented in various ways. The invention and its embodiments are not limited to the examples described above but may vary within the scope of the claims.

The invention claimed is:

1. A method of sensitizing a gram-negative bacterium or reducing build-up of resistance of a gram-negative bacterium towards an antimicrobial agent by exposing the microbe to a pillararene and the antimicrobial agent.

2. The method according to claim 1, wherein the pillararene is a pillar[5]arene or a salt thereof.

3. The method according to claim 2, wherein the pillar [5]arene is 4,9,14,19,24,26,28,30,32,34-Deca[2-(trimethylamin-io) ethoxy]hexacyclo[21.2.2.$2^{3,6}$.$2^{8,11}$.$2^{13,16.21,8,21}$] pentatriaconta1(25),3,5,8,10,13,15,18,20,23,26,28,30,32, 34-pentadecaene·10bromide.

4. The method according to claim 1, wherein the Gram-negative bacterium belongs to genera *Pseudomonas* and *Acinetobacter.*

5. The method according to claim 1, wherein the antimicrobial agent is selected from β-lactams, aminoglycosides, fluoroquinolones, macrolides, tetracyclines, novobiosin, chloramphenicol, ethidium bromide and colistin.

6. A method of inhibiting and/or treating and/or preventing a microbial infection in a subject having a microbial infection or being at risk of a microbial infection or formation of a biofilm by a gram-negative bacterium in the subject by administering an antimicrobial agent and a pillararene to the subject.

7. The method according to claim 6, wherein the pillararene is a pillar[5]arene or a salt thereof.

8. The method according to claim 7, wherein the pillar [5] arene is 4,9,14,19,24,26,28,30,32,34-Deca [2-(trimethylamin-io) ethoxy] hexacyclo [21.2.2.$2^{3,6}$.$2^{8,11}$.$2^{13,16.21,8,21}$] pentatriacontal (25),3,5,8,10,13,15,18,20,23,26,28,30,32, 34-pentadecaene·10bromide.

9. The method according to claim 6, wherein the Gram-negative bacterium belongs to genera *Pseudomonas* and *Acinetobacter.*

10. The method according to claim 6, wherein the microbial infection is an acute infection or the infection is caused by planktonic microbes.

11. The method according to claim 6, wherein the antimicrobial agent is selected from β-lactams, aminoglycosides, fluoroquinolones, macrolides, tetracyclines, novobiosin, chloramphenicol, ethidium bromide and colistin.

12. The method according to claim 6, wherein the microbial infection is a pulmonary infection.

13. The method according to claim 6, wherein the microbial infection relates to cystic fibrosis.

14. The method according to claim 6, wherein the pillararene, or a salt thereof, is administered to the subject before, during, or after a treatment with the antimicrobial agent.

* * * * *